United States Patent
Matson

(10) Patent No.: US 6,210,970 B1
(45) Date of Patent: *Apr. 3, 2001

(54) METHOD OF DIAGNOSING OR CATEGORIZING DISORDERS FROM BIOCHEMICAL PROFILES

(75) Inventor: Wayne R. Matson, Ayer, MA (US)

(73) Assignee: ESA, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/092,543

(22) Filed: Jul. 16, 1993

Related U.S. Application Data

(63) Continuation of application No. 07/643,541, filed on Jan. 18, 1991, now abandoned, which is a continuation-in-part of application No. 07/274,505, filed on Nov. 21, 1988, now Pat. No. 5,104,639, which is a division of application No. 06/797,615, filed on Nov. 13, 1985, now Pat. No. 4,863,873, which is a continuation of application No. 06/670,483, filed on Nov. 13, 1984, now abandoned, which is a continuation-in-part of application No. 06/579,401, filed on Feb. 17, 1984, now Pat. No. 4,511,659, which is a continuation-in-part of application No. 06/472,387, filed on Mar. 4, 1983, now abandoned, which is a continuation-in-part of application No. 06/425,183, filed on Sep. 28, 1982, now abandoned, which is a continuation of application No. 06/111,917, filed on Jan. 14, 1980, now Pat. No. 4,404,065.

(51) Int. Cl.$^7$ ................................................ G01N 33/48
(52) U.S. Cl. ............................ 436/64; 436/63; 436/150; 436/161
(58) Field of Search ............................ 436/63, 64, 150, 436/161, 424, 73, 204; 424/2, 520, 530, 531, 532, 545; 73/61.52, 61.59; 204/153.1, 403, 406

(56) References Cited

U.S. PATENT DOCUMENTS 4,338,811 * 7/1982 Mivagi et al. ........................ 73/23.1
4,343,767 * 8/1982 Long et al. ............................. 422/70
4,511,659 * 4/1985 Matson ................................ 422/70 X
4,654,313 * 3/1987 Hartman ............................ 436/804 X
4,863,873 * 9/1989 Matson .................................. 436/63
5,104,639 * 4/1992 Matson ............................... 436/150 X

OTHER PUBLICATIONS

Dorland et al, "Dorland's Illustrated Medical Dictionary", 1988, p. 461, W.B. Saunders Company.*
M. Flint Beal et al. *J. Neurol.* 1990, 55, 1327–1339.*
T. Takeshima et al. *Chem. Abstr.* 1991, 115, 25237p.*
W.R. Matson et al, *Chem. Abstr.* 1991, 115, 204085j.*
E.D. Bird et al. *Chem. Abstr.* 1991, 115, 205021x.*
C. Banissi–Sabourdy et al. *Bioelectrochem. Bioenerg.* 1992, 28, 127–147.*
K.O. Ash et al. *Am. J. Clin. Path.* 1983, 79, 574–581.*
S. Ito et al. *Clin. Chem,* 1985, 31, 1185–1188.*

(List continued on next page.)

*Primary Examiner*—Arlen Soderquist
(74) *Attorney, Agent, or Firm*—Hayes, Soloway, Hennessey, Grossman & Hage, P.C.

(57) ABSTRACT

A method for diagnosing disorders in a subject organism, in which fluid samples from normal and abnormal organisms are analyzed to generate electrical signal patterns representative of molecular constituents of the samples. A data base of electrical signal patterns representative of frequency distribution of sample constituents from the abnormal organisms having known categories of disorders and control samples from normal organisms are created, and a fluid sample taken from the subject organism is analyzed by comparing it to the data base for conformity to the electrical signal patterns representative of the frequency distribution. The invention has particular applicability to assisting in the diagnosis of degenerative diseases such as Alzheimer's Disease, Parkinson's Disease, Huntington's Disease, schizophrenia, amyotrophic lateral sclerosis and Progressive Supernuclear Palsy.

20 Claims, 4 Drawing Sheets

OTHER PUBLICATIONS

L. Volicer et al. *Arch. Neurol.* 1985, 42, 1158–1161.*
B. Seltzer et al. *Arch. Neurol.* 1986, 43, 665–668.*
A. Foti et al. *Clin. Chem.* 1987, 33, 2209–2213.*
W.R. Matson et al. *Life Sci.* 1987, 41, 905–908.*
J.B. Lucot et al. *Life Sci.* 1989, 43, 1239–1245.*
P.E. Milbury et al *Neurobiol. Aging.* 1990, 11, 336–345.*
H.D. Stowe et al. *Am. J. Vet. Res.* 1985, 46, 561–565.*
J.S. Amenta et al. *Clin. Chem.* 1987, 33, 647–652.*
W.R. Matson et al. *Adv. Behav. Biol.* 1990, 38A, 513–516.*
E.D. Bird et al. *Adv. Behav. Biol.* 1990, 38A, 529–536.*
T. Takeshima et al. *Iryo.* 1990, 44, 484–490.*
M.W. O'Halloran et al. *Clin. Chim. Acta* 1970, 27, 23–46.*
N. Ressler *Persp. Biol. Med.* 1975, 19, 101–117.*

* cited by examiner

METHOD OF DIAGNOSING OR CATEGORIZING DISORDERS FROM BIOCHEMICAL PROFILES

This is a continuation of application Ser. No. 07/643,541 filed on Jan. 18, 1991 (now abandoned).

This application is in part a continuation of my application Ser. No. 07/274,505, filed Nov. 11, 1988 now U.S. Pat. No. 5,104,639, which in turn is a divisional application of my Ser. No. 06/797,615, filed Nov. 13, 1985 (Now U.S. Pat. No. 4,863,873), which is in turn a continuation of my application Ser. No. 06/670,483, filed Nov. 13, 1984 (now abandoned), which in turn is in part a continuation of my application Ser. No. 06/579,401, filed Feb. 17, 1984 (now U.S. Pat. No. 4,511,659), which is in part a continuation of my application Ser. No. 06/472,387 filed Mar. 4, 1983 (now abandoned), and in part a continuation of my application Ser. No. 06/425,183 filed Sep. 28, 1982 (now abandoned), which is in turn a continuation of my application Ser. No. 06/111,917 filed Jan. 14, 1980 (now U.S. Pat. No. 4,404,065).

This invention relates to analytical and mathematical methods for diagnosing or categorizing disorders. The invention has particular utility for diagnosing or categorizing disorders in living animals from analysis profiles of biologically active materials such as neurotransmitters and other neurochemical substances in brain tissue, cerebrospinal fluid, plasma, serum, saliva, blood containing platelets, nasal mucosa, urine and the like, such as catecholamines, their precursors, cofactors and their metabolites. The invention is uniquely capable of differentiating a large number of compounds of biological, diagnostic and/or pharmaceutical significance and of using such differential for diagnosing disorders and will be described in connection with such utility although other uses are contemplated.

There is an extensive body of literature relating abnormalities in neurotransmitters, precursors, and metabolites to degenerative, neuropsychiatric and behavioral disorders, hypertension and certain carcinomas. See, for example, Schildkraut et al in *The Brain, Biochemistry and Behavior*, Proceedings of the Sixth, Arnold O. Beckman Conference in Clinical Chemistry, pages 47–68. Although the potential role of these compounds in a number of significant disorders has been established, their routine analysis has not yet achieved widespread clinical use. Two problems in the clinical utility of neurotransmitter measurements are related to the economic and technical limitations of current technology. First, there is felt to be a high degree of interlaboratory and intersample uncertainty in quantitative values. Second, it has been difficult to measure enough of the known metabolically related compounds of a particular neurotransmitter to fully describe its biochemical significance in an individual sample, or to detect, identify and measure unusual neurotransmitters—an important aspect of basic research in various disease states that is presently very expensive and specialized.

While a number of interlaboratory technique intercomparisons for a variety of neurotransmitters have been carried out, there has been no comprehensive study within and among different techniques and laboratories for neurotransmitters in typical samples of interest. In the absence of such studies, given the complexity of the analytical problem and the historically wide variation whenever an analyte has been subjected to rigorous interlaboratory testing, the current values for normal and abnormal neurotransmitter levels must be taken with unspecified and probably wide limits of confidence.

Although the analysis of single neurotransmitters or metabolites from a complex biochemical pathway has been shown to correlate with a number of disorders utilizing statistical analysis over a large number of samples, the analytical level of a single neurotransmitter in an individual sample, with a few exceptions, has had relatively low clinical diagnostic utility. Essentially the state of the field of biochemical correlates of disorders is that while between large populations of normal and abnormal individuals a correlation generally can be determined for a particular biochemical, the scatter that results from both analytical and biochemical phenomena typically does not permit the level of a particular biochemical to be utilized diagnostically for a particular single individual. Nor may a single biochemical value be utilized for the rational prescription or development of a pharmaceutical for that individual. This is not particularly surprising in that both the levels and effects of a particular neurotransmitter are modified by a number of other neurotransmitters, in the same, or parallel metabolic pathways. If, for instance, 5-HT (serotonin) is to be used as a diagnostic tool for depression, suicidal tendencies, or schizophrenia, it would be necessary and perhaps provide a route to definitive diagnosis and pharmaceutical specification or development, to simultaneously determine the approximately 40 other compounds that derive from tryptophan and significantly effect the indolaminergic neuronal system's activity.

In recent years, LCEC (Liquid Chromotography with Electrochemical Detection) has become a common tool for the determination of catecholamines biogenic amines and their metabolites in biological fluids. Because of sensitivity limitations (typically 20–50 pg) and the complexity of biological samples, both separation and concentration steps typically have been necessary. Heretofore, plasma catecholamine analysis typically required three steps. First, the sample is collected and the catecholamines separated and concentrated, for example, using the alumina extraction procedure of Anton and Sayre (See A. H. Anton and D. F. Sayre, J. Pharmacol, Exp. Ther., 138 (1962), p. 360–375). The analytes, norepinephrine, epinephrine and dopamine, along with the internal standard DHBH (dihydroxybenzylamine), then are separated chromatographically, and finally detected electrochemically. Typical sample size requirements are 1.0 ml plasma or serum. In routine clinical use, there have been numerous problems with conventional techniques (alumina absorption, ion exchange and extraction), due to a large number of poorly understood variables, in the overall analysis system of sample acquisition, storage, preparation and sensor response. These problems have quite likely confused the relationships that may exist between levels and distribution of the catecholamines and various physiological and behavioral phenomena and disease states.

In the analysis of complex biological materials such as blood, serum and cerebrospinal fluids which may contain numerous different constituents, the important (e.g. abnormal) metabolites such as neurotransmitters to be identified may be present in only parts per trillion. While a chromatographic column can achieve macro separation of the various constituents, it may not provide adequate spatial (in time) separation of the extremely small portion of metabolites of interest from the much larger percentage of the many other compounds coeluted from the column at the same time as the metabolites of interest. Many of these interfering coeluted materials are electrochemically active but electrochemically irreversible, while many metabolites such as neurotransmitters are both electrochemically active and electrochemically reversible. It has been found that the analytical problems of reliable measurements of neurochemicals and related compounds are complicated by the fact that interferences with conventional or prior technologies are disorder related. This was discussed in my prior publication, (Matson et al, Clinical Chemistry, Vol. 30, No. 9, 1984) (see U.S. Pat. No. 4,511,659) for dopamine, dopac and seratonin measurements in directly analyzed brain extract anti cerebrospinal fluid for normal, schizophrenics and Alzheimers. Recent work has indicated that even for the widely used and accepted technique of alumina extraction for plasma catecholamines that interferences may be disorder specific. Higher values for Norepinephrine (NE) and Epinephrine (EP) were observed following alumina extraction and analysis of a single energy conventional electrochemical detector than for a three cell redox detector on neonatal stress blood samples. Analysis of the neonate extracts on the sixteen channel chemical imaging system revealed several unexpected compounds that are potential interferences including dihydroxyphenylacetic acid (DOPAC), 3 hydroxykynurenamine (3-OHKYA) and 3-hydroxy-anthranilic acid (3-OHAN). These compounds have not been detected in normal adult plasma alumina extracts.

In my aforesaid U.S. Pat. No. 4,511,659, there is provided an electrochemical detection system comprising a plurality of coulometrically efficient electrochemical cells, in series, for sequentially oxidizing and reducing selected substances in a sample solution under controlled conditions prior to measurement on a downstream testing electrode or electrodes. More specifically, in accordance with the invention provided in my aforesaid U.S. Pat. No. 4,511,659, a sample solution (e.g. a body fluid) is passed through a suitable chromatographic column and the eluant is streamed in contact with a series of electrochemically isolated, in-line coulometric electrodes operated under conditions so as to establish a series of "gates" for the sequential oxidation and reduction of substances in the sample solution whereby to screen (remove) selected interfering and electrochemically irreversible substances contained in the sample solution, while passing selected electrochemically reversible products for detection and measurement on a downstream electrode. The gate electrode series is follows in-line by one or more, preferably an array of six or more coulometric measuring electrodes, each formed of porous electrode base material such as fritted graphite, fritted carbon or other conductive fritted material, for detecting and measuring the electrochemically reversible compounds of interest (e.g. neurotransmitters).

As reported in my aforesaid U.S. Pat. No. 4,511,659, there are several beneficial effects of this approach to electrochemical analysis. Long-term drift in response is effectively eliminated by acquiring essentially 100% of the signal. The capability of analyzing essentially 100% of a material allows the assay of compounds of unknown purity by relating them to the basic principles of electrochemical reaction embodied in Faraday's Law. Poisoning of the electrode, a dominant problem with electrochemical sensors, is effectively eliminated by the use of a much larger relative surface area for reaction. And, finally, and most important to the eventual development of array and gate cells, a coulometric electrode by virtue of its essentially 100% efficiency allows sequential oxidation and/or reduction of compounds at successive-in-line detectors. The improved sensitivity of the detection system as discussed in my aforesaid U.S. Pat. No. 4,511,659, particularly where two or more active testing electrodes follow the screening electrodes has given the ability to do direct injections of serum filtrates and has also allowed the generation of reproducible patterns of compounds with catecholamine like electrochemical behavior of a large number of resolvable components. This provides the possibility of performing pattern recognition for the diagnosis or perhaps even predictive diagnosis, of various disorders or disease states.

In my copending application Ser. No. 797,615 and its parent U.S. Pat. No. 4,863,873, I describe a system for resolving and detecting hundreds of compounds in a single sample at femtogram levels whereby to provide a small molecule inventory or metabolic pathway pattern of an individual. As taught in my aforesaid U.S. Pat. No. 4,863,873, the small molecule inventory may be considered to reflect the underlying activity and distribution of the enzymatic pathways of an individual and hence reflect an operational measure of the genome determining those enzymes. The small molecule inventory of an individual may thus be used to determine the health state of the individual and/or to diagnose disease states. Correlation of the patterns from a plurality of individuals provides an understanding of the mechanisms of disorders or disease states or conditions and, in turn, provides a rational route to pharmacological development leading to treatment, cure or suppression of such disorders, disease states or conditions.

The present invention is an improvement in the invention described in my aforesaid U.S. Pat. No. 4,863,873. More particularly, in the practice of my invention as described in my U.S. Pat. No. 4,863,873, I have observed that the biochemical analysis profiles of "normal" or healthy individuals may vary quite widely, while the biochemical profile analysis data of individuals having disorders is far less chaotic. More particularly, I have observed that the frequency distribution of certain biochemical compounds or ratios of compounds in individuals suffering from a disorder are far less chaotic than "normal" or healthy individuals. This leads to a general protocol for diagnosing, categorizing or differentiating individuals based on comparisons of biochemical analytical data of small molecule inventory against data bases of known or previously diagnosed cases. By way of example the process of the present invention may advantageously be employed in the differentiation of neurological degenerative dementing or affective disorders such as Alzheimer's disease, Huntington's disease, Parkinson's disease, schizophrenia, or Progressive Supernuclear Palsy from each other and neurologically normal controls. Moreover, by suitable selection of variables, the process of the present invention also is applicable to classification of tumors, carcinomas, cardiovascular abnormalities and other disorders. Similarly, the process of the present invention advantageously may be utilized to select therapy based on categories of known successful vs. unsuccessful outcomes.

While not wishing to be bound by theory, the two fundamental hypotheses underlying the process of the present invention are:

1. The underlying genetic makeup or predis-position of an individual will reflect through the proteins, enzymes, and other factors it determines in patterns of small molecules. Individual components within these patterns will be affected by environmental effects such as diet, stress or chemical inset; however, the overall pattern of relationships will reflect the underlying operation of the genome or the interference of a particular disorder. Among the small molecules are the transmitters, cofactors and metabolites that regulate neuronal and endocrine functions and the interactions of somatic and central nervous system processes. Thus, the compounds such as purines, tyrosine and tryptophan derived neurotransmitters, peptides, pterin and vitamine cofactors are highly relevant to the effect or etiology of neurological disorders, cardiovascular disfunction and certain tumors or carcinomas.

2. The relationships of these biochemical patterns from a disorder are less chaotic or more regular than those from healthy controls. All of the biochemical systems of small molecules are interconnected and interrelated in a complex web of feedback and response. These interactions are highly nonlinear and thus, depending on subtle differences in initial conditions, the response of individual components in a biochemical pattern will be highly variable. The overall system will thus behave in a mathematically chaotic fashion. In a disorder, elements within the biochemical pattern are over or underregulated, thus reducing the degrees of freedom or overall variability. Consequently, the presence of a disorder implies more regulated or less chaotic variability of compounds or relationships among compounds in patterns from disordered individuals.

These two fundamental hypotheses provide an approach to diagnostic categorization of disorders using frequency distributions of compounds and relationships from large data bases (which may be of epidemiologically significant size).

DESCRIPTION OF THE DRAWINGS

For a fuller understanding of the nature and objects of the present invention, reference should be had to the following detailed description taken in combination with the accompanying drawings wherein.

DETAILED DESCRIPTION OF THE INVENTION

Figure 1A:
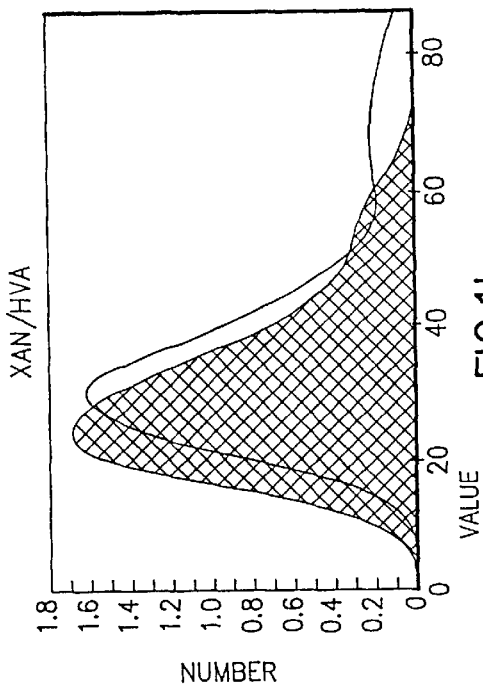
FIGS. 1a–1d are plots showing frequency measurement distributions.
Figure 1B:
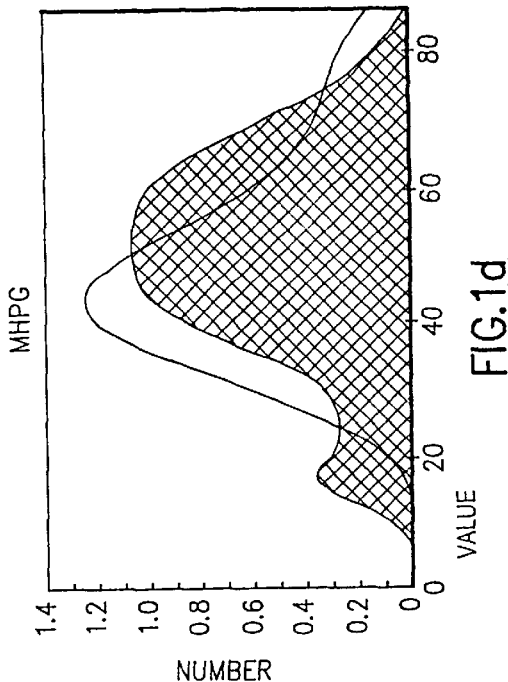
Figure 1C:
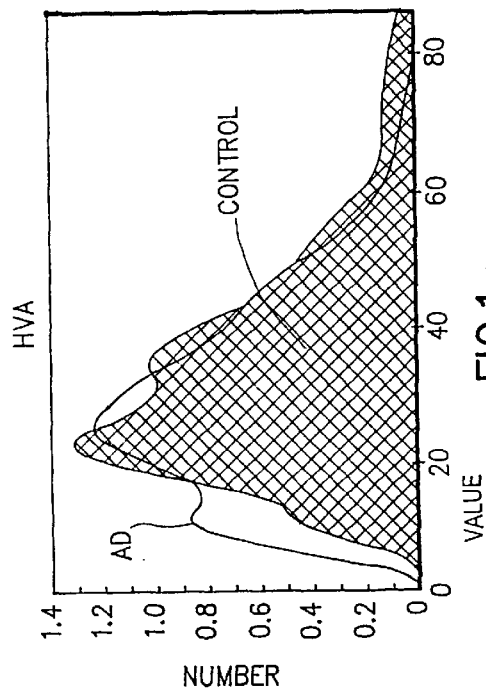
Figure 1D:
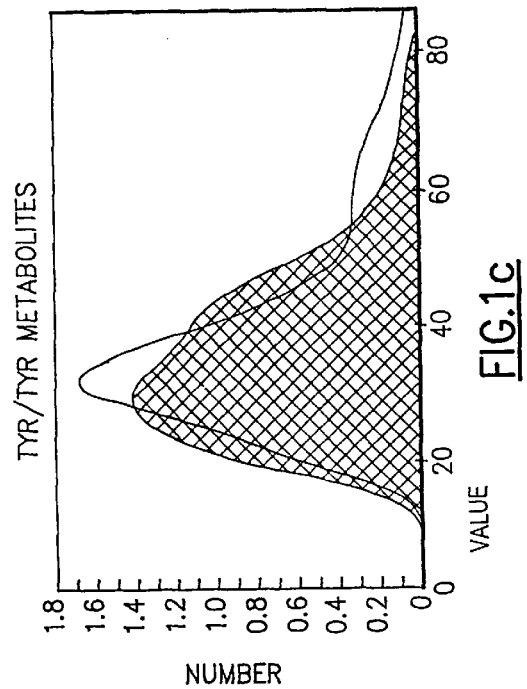

Methodology for Sample Analysis and Data Base Creation 280 cerebrospinal fluid (CSF) samples from the categories Alzheimer's Disease—AD (61 samples), Parkinson's Disease—PD (60 samples), schizophrenia—SC (60 samples), Huntington's Disease—HD (20 samples), Supernuclear Palsy—PSP (13 samples) and neurologically normal controls—C (68 samples), were electrochemically analyzed in accordance with the teachings of my aforesaid U.S. Pat. No. 4,863,873. Samples from normal and diseased individuals were prepared and flowed through a chromatographic column, and detected in an electrochemical cell using an NCA Chemical Analyzer, Model No. CEAS available from ESA, Inc., Bedford, Mass. All samples were from 7th or 8th mL aliquots of nostril caudal gradients. Pools were created for each category utilizing small subaliquots of the samples, and pools of all samples were created for analytical quality control and evaluation of unknowns. Samples were run under a variant of a standard reverse phase gradient procedure (Table 1) in the repetitive sequence Control Standard, Pool, 7 Samples, Control Standard, Pool, . . . as set forth in Table I:

TABLE I

REAL TIME SETUP REVIEW

|   | TIME | DEVICE | FUNCTION | VALUE | TOTAL |
|---|------|--------|----------|-------|-------|
| 1 | 0.00 | FLOW | %B | 5 | 1.20 |
| 2 | 0.20 | CLEAN CELL | ON | 960 | |
| 3 | 0.50 | CLEAN CELL | OFF | | |
| 4 | 7.00 | AUTO ZERO | ON | | |
| 5 | 7.20 | FLOW | %B | 5 | 1.20 |
| 6 | 7.58 | AUTO SAMPLER | INJECT | | |
| 7 | 8.00 | FILE | START | | |
| 8 | 66.00 | FLOW | %B | 94 | 1.06 |
| 9 | 66.00 | FLOW | %B | 5 | 1.20 |
| 10 | 70.00 | FILE | STOP | | |
| 11 | 70.00 | FLOW | %B | 5 | 1.20 |
| 12 | 70.00 | AUTO SAMPLER | STEP | | |
| 13 | 70.00 | END | | 2 | |
| 14 | 70.00 | METHOD | M147 | | |

REVIEW OF LIVE METHOD

| Full Scale Current | | | | P'stats | | | | Autorange On |
|---|---|---|---|---|---|---|---|---|
| 10 uA | 100 uA | 10 uA | 10 uA | −40 mV | 25 mV | 90 mV | 155 mV | |
| 1 uA | 1 uA | 10 uA | 1 uA | 220 mV | 285 mV | 350 mV | 415 mV | Floor |
| 1 uA | 1 uA | 1 uA | 1 uA | 480 mV | 545 mV | 610 mV | 675 mV | 100 nA |
| 1 uA | 1 uA | 1 uA | 1 uA | 740 mV | 805 mV | 870 mV | 910 mV | |

Cell Box Temp: 35° C.

| | UPPER LIMIT | LOWER LIMIT |
|---|---|---|
| PUMP A: | 350 | 0 |
| PUMP B: | 350 | 0 |
| VALVE: POS1 | | |

TABLE II

Sat. Nov. 18 17:15:22 1990
        Standard    std0001
Table: NOY8STD
Study: CSFRUX01
Identified Compounds in Standard: 38
Missing Compounds in Standard: 0

| # | File RT | Name Conc | 1 | 2 | 3 | 4 | 5 | 6 | 7 |
|---|---------|-----------|---|---|---|---|---|---|---|
| 1 | std0001 1.725 | ASC 10000.00 | 1.717 3872279 | 1.700 9625125 | 1.725 1.27e+07 | 1.725 1.60e+07 | 1.750 1.50e+07 | 1.733 1.14e+07 | |
| 2 | std0001 2.283 | CYS 1000.00 | | | | | | | 2.267 129467 |
| 3 | std0001 2.350 | URIC 0000.00 | | | 2.333 5672 | 2.342 1324197 | 2.350 3193191 | 2.350 1019128 | |
| 4 | std0001 3.058 | XAM 1000.00 | | | | | | | |
| 5 | std0001 3.125 | HX 100.00 | | | | | | | |
| 6 | std0001 4.875 | VMA 10.00 | | | | 4.883 387 | 4.867 4959 | 4.875 16674 | 4.875 13957 |
| 7 | std0001 4.900 | GSH 500.00 | | | | | | | 4.875 13957 |
| 8 | std0001 5.642 | NE 10.00 | 5.625 334 | 5.642 18928 | 5.642 17463 | 5.650 1507 | 5.650 117 | | |
| 9 | std0001 6.075 | MHPG 10.00 | | | | | | 6.075 749 | 6.075 13983 | 6.075 5545 |

| # | File RT | Name Conc | 8 | 9 | 10 | 11 | 12 | 13 | 14 | 15 | 16 |
|---|---------|-----------|---|---|----|----|----|----|----|----|----|
| 1 | | | | | | | | | | | |
| 2 | std0001 2.283 | CYS 1000.00 | 2.267 251043 | 2.258 528682 | 2.267 1298734 | 2.275 1601456 | 2.283 2250767 | 2.292 1062584 | | | |
| 4 | std0001 3.058 | XAM 1000.00 | | 3.042 47171 | 3.033 1393667 | 3.058 3304889 | 3.067 2039171 | 3.067 350667 | 3.108 110609 | | |
| 5 | std0001 3.125 | HX 100.00 | | | | | | | 3.108 110609 | 3.117 154070 | 3.125 161138 |
| 6 | | | | | | | | | | | |
| 7 | std0001 4.900 | GSH 500.00 | 4.875 28075 | 4.875 51532 | 4.875 117237 | 4.892 133772 | 4.900 197987 | 4.988 85618 | | | |
| 8 | | | | | | | | | | | |
| 9 | std0001 6.075 | MHPG 10.00 | 6.075 1828 | 6.083 1718 | 6.092 1044 | | | | | | |

| # | File RT | Name Conc | 1 | 2 | 3 | 4 | 5 | 6 | 7 |
|---|---------|-----------|---|---|---|---|---|---|---|
| 10 | std0001 6.392 | HGA 10.00 | 6.392 16607 | 6.408 4976 | | | | | |
| 11 | std0001 7.942 | G 100.00 | | | | | | | |
| 12 | std0001 9.150 | GR 500.00 | | | | | | | |
| 13 | std0001 9.283 | LD 10.00 | 9.325 165 | 9.283 10336 | 9.283 14158 | 9.292 1156 | 9.275 562 | | |
| 14 | std0001 9.650 | MET 500.00 | | | | | | | |
| 15 | std0001 10.008 | AM 100.00 | | | | 10.008 33745 | 10.008 118573 | 10.017 17512 | 10.000 2128 |
| 16 | std0001 10.142 | EPI 10.00 | 10.167 367 | 10.142 14152 | 10.150 9783 | | | | |
| 17 | std001 10.217 | EPI A 100.00 | | | | | | | |
| 18 | std0001 11.833 | DOPAC 10.00 | 11.825 247 | 11.833 7794 | 11.833 9749 | 11.842 1412 | 11.850 445 | 11.833 251 | |

| # | File RT | Name Conc | 8 | 9 | 10 | 11 | 12 | 13 | 14 | 15 | 16 |
|---|---------|-----------|---|---|----|----|----|----|----|----|----|
| 10 | | | | | | | | | | | |
| 11 | std0001 7.942 | G 100.00 | | 7.942 2395 | 7.942 122100 | 7.950 53287 | 7.958 4420 | 7.958 975 | | | |
| 12 | std0001 9.150 | GR 500.00 | | | 9.142 859 | 9.133 26558 | 9.125 194121 | 9.142 430593 | 9.150 1054244 | 9.175 189936 | 9.192 111915 |
| 13 | | | | | | | | | | | |
| 14 | std0001 9.650 | MET 500.00 | | | 9.642 986 | 9.642 6461 | 9.650 26013 | 9.650 33548 | 9.650 107832 | 9.667 86595 | 9.675 31459 |

TABLE II-continued

Sat. Nov. 18 17:15:22 1990
          Standard    std0001
Table: NOY8STD
Study: CSFRUX01
Identified Compounds in Standard: 38
Missing Compounds in Standard: 0

15
16
17 std001  EPI      A                                                              10.250  10.217
   10.217  100.00                                                                   26046   36349
18

| #  | File RT | Name Conc | 1 | 2 | 3 | 4 | 5 | 6 | 7 |
|----|---------|-----------|---|---|---|---|---|---|---|
| 19 | std0001 13.200 | 3OHAN 10.00 | | 13.225 1194 | 13.200 29905 | 13.217 8215 | 13.242 2107 | 13.250 1401 | |
| 20 | std001 13.200 | 3OHXY 10.00 | | 13.225 1194 | 13.200 29905 | 13.217 8215 | 13.242 2107 | 13.250 1401 | |
| 21 | std0001 13.450 | 4HPLA 100.00 | | | | | | | |
| 22 | std0001 13.692 | XMN 10.00 | | | | | 13.683 1593 | 13.692 14780 | 13.683 3917 |
| 23 | std0001 13.992 | 4HBAC 200.00 | | | | | | | |
| 24 | std0001 15.233 | TYR 1000.00 | | | | | | | 15.250 232 |
| 25 | std0001 15.592 | 5HTP 10.00 | | | 15.583 6994 | 15.592 16297 | 15.617 463 | | |
| 26 | std0001 17.342 | DA 10.00 | | 17.342 17722 | 17.342 6301 | 17.358 305 | 17.367 144 | 17.375 8313964 | |
| 27 | std0001 17.892 | SHIAA 50.00 | | 17.850 233 | 17.892 9330 | 17.892 119759 | 17.908 14604 | 17.925 549 | |

| #  | File RT | Name Conc | 8 | 9 | 10 | 11 | 12 | 13 | 14 | 15 | 16 |
|----|---------|-----------|---|---|----|----|----|----|----|----|----|
| 19 | | | | | | | | | | | |
| 20 | | | | | | | | | | | |
| 21 | std0001 13.450 | 4HPLA 100.00 | | 13.442 13364 | 13.450 125434 | 13.467 43118 | 13.458 2233 | | | | |
| 22 | | | | | | | | | | | |
| 23 | std0001 13.992 | 4HBAC 200.00 | | | | 13.983 75738 | 13.992 207495 | 13.992 311864 | 14.008 170423 | | |
| 24 | std0001 15.233 | TYR. 1000.00 | 15.242 3866 | 15.225 102584 | 15.233 1181673 | 15.250 776764 | 15.250 117510 | 15.292 | | | |
| 25 | | | | | | | | | | | |
| 26 | | | | | | | | | | | |
| 27 | | | | | | | | | | | |

| #  | File RT | Name Conc | 1 | 2 | 3 | 4 | 5 | 6 | 7 |
|----|---------|-----------|---|---|---|---|---|---|---|
| 28 | std0001 18.100 | 4HPAC 200.00 | | | | | | | 18.083 80 |
| 29 | std0001 18.117 | KYA 50.00 | | | | | | | |
| 30 | std0001 31.608 | 3OMD 10.00 | | | | 21.575 58 | 21.608 2183 | 21.608 11535 | 21.600 2176 |
| 31 | std0001 22.200 | 5HTOL 10.00 | | 22.167 47 | 22.200 1668 | 22.200 19401 | 22.217 1931 | | |
| 32 | std00l 23.917 | HVA 200.00 | | | | 23.925 225 | 23.925 13994 | 23.917 237705 | 23.917 163964 |
| 33 | std0001 24.258 | KYX 100.00 | | | | | | | |
| 34 | std0001 24.492 | TYRA 80.00 | | | | | | | |
| 35 | std0001 30.792 | 5HT 10.00 | | 30.742 231 | 30.783 6955 | 30.792 9627 | | | |
| 36 | std0001 31.975 | 3HT 100.00 | | | | 31.967 143 | 31.975 11501 | 31.975 33026 | 31.967 2425 |

| #  | File RT | Name Conc | 8 | 9 | 10 | 11 | 12 | 13 | 14 | 15 | 16 |
|----|---------|-----------|---|---|----|----|----|----|----|----|----|
| 28 | std0001 18.100 | 4HPAC 200.00 | 18.117 1143 | 18.092 37258 | 18.100 461257 | 18.125 287050 | | | | | |
| 29 | std0001 | KYA | | | | | | 18.075 | 18.117 | 18.167 | 18.175 |

TABLE II-continued

Sat. Nov. 18 17:15:22 1990
Standard std0001
Table: NOY8STD
Study: CSFRUX01
Identified Compounds in Standard: 38
Missing Compounds in Standard: 0

| | | | | | | | | | | | |
|---|---|---|---|---|---|---|---|---|---|---|---|
| | 18.117 | 50.00 | | | | | | 59412 | 112086 | 54548 | 38306 |
| 30 | std0001 | 30MD | 21.592 | | | | | | | | |
| | | | 143 | | | | | | | | |
| 31 | | | | | | | | | | | |
| 32 | std0001 | HVA | 23.925 | 23.925 | 23.950 | | | | | | |
| | | | 47372 | 8852 | 2293 | | | | | | |
| 33 | std0001 | KYX | | | | 24.267 | 24.258 | 24.283 | 24.300 | 24.308 | 24.308 |
| | 24.258 | 100.00 | | | | 101620 | 108998 | 55261 | 39928 | 21718 | 4609 |
| 34 | std0001 | TYRA | | 24.475 | 24.492 | 24.517 | | | | | |
| | 24.492 | 80.00 | | 2368 | 28935 | 5390 | | | | | |
| 35 | | | | | | | | | | | |
| 36 | std0001 | 3MT | 31.975 | | | | | | | | |
| | | | 171 | | | | | | | | |

| # | File<br>RT | Name<br>Conc | 1 | 2 | 3 | 4 | 5 | 6 | 7 |
|---|---|---|---|---|---|---|---|---|---|
| 37 | std0001 | TPOL | | | | | | | 41.500 |
| | 41.467 | 10.00 | | | | | | | 375 |
| 38 | std0001 | TRP | | | | | 45.350 | 45.342 | 45.388 |
| | 45.292 | 700.00 | | | | | 615 | 8371 | 23358 |

| # | File<br>RT | Name<br>Conc | 8 | 9 | 10 | 11 | 12 | 13 | 14 | 15 | 16 |
|---|---|---|---|---|---|---|---|---|---|---|---|
| 37 | std0001 | TPOL | 41.475 | 41.458 | 41.467 | 41.492 | | | | | |
| | 41.467 | 10.00 | 2006 | 7109 | 9905 | 4810 | | | | | |
| 38 | std0001 | TRP | 45.300 | 45.275 | 45.292 | 45.325 | 45.350 | 45.350 | | | |
| | 45.292 | 700.00 | 248497 | 967515 | 2056846 | 1090677 | 187013 | 109610 | | | |

TABLE III

Tue Dec 18 11:43:57 1990
Sample Report Page 1
Sample: POOL37
Standard:
Table: POOL19A
Study: CSF19A
Compounds identified: 22
Known Compounds Not Found: 0
Unknown Peak Clusters: 745
<u>Compounds Identified</u>

| Com-<br>pound | Conc | RT | RT Error | Height | Ratio Accuracy |
|---|---|---|---|---|---|
| *p01 | 104.413971 | 2.617 | 0.100 | 167971 | 7/6<br>0.999 |
| XAN | 973.750732 | 2.900 | 0.117 | 756026 | 10/11 12/11<br>0.861 0.959 |
| *p02 | 101.869156 | 3.108 | 0.125 | 208822 | 15/16<br>0.666 |
| p03 | 131.687439 | 5.733 | 0.275 | 2747 | |
| p04 | 106.228569 | 8.242 | 0.325 | 142085 | 13/14 15/14<br>0.977 0.891 |
| TYR | 979.260254 | 13.567 | 0.692 | 1375195 | 9/10 11/10<br>0.987 0.977 |

TABLE III-continued

Tue Dec 18 11:43:57 1990
Sample Report Page 1
Sample: POOL37
Standard:
Table: POOL19A
Study: CSF19A
Compounds identified: 22
Known Compounds Not Found: 0
Unknown Peak Clusters: 745
<u>Compounds Identified</u>

| Com-<br>pound | Conc | RT | RT Error | Height | Ratio Accuracy |
|---|---|---|---|---|---|
| *P05 | 99.553802 | 14.633 | 0.583 | 52515 | 13/14<br>0.949 |
| P09 | 89.990860 | 15.117 | 0.650 | 7632 | 9/10 11/10<br>0.850 0.923 |
| P07 | 92.967072 | 15.275 | 0.600 | 55664 | 14/15<br>0.951 |
| P08 | 96.659180 | 16.133 | 0.417 | 29579 | 10/11<br>0.976 |
| *P10 | 96.603462 | 21.875 | 0.942 | 42516 | 9/10<br>0.949 |
| HVA | 195.139450 | 22.475 | 0.800 | 30508 | 5/6 7/6<br>0.987 0.921 |

TABLE III-continued

Tue Dec 18 11:43:57 1990
Sample Report Page 1
Sample: POOL37
Standard:
Table: POOL19A
Study: CSF19A
Compounds identified: 22
Known Compounds Not Found: 0
Unknown Peak Clusters: 745
Compounds Identified

| Compound | Conc | RT | RT Error | Height | Ratio | Accuracy |
|---|---|---|---|---|---|---|
| P11 | 102.689194 | 24.892 | 0.717 | 16233 | 16/15 | 0.892 |
| P12 | 91.103188 | 25.150 | 0.850 | 10652 | 9/10 | 0.951 |
| *p18 | 98.121086 | 26.850 | 1.308 | 470 | | |
| *p19 | 121.804512 | 27.192 | 1.142 | 324 | | |
| P13 | 96.415916 | 28.158 | 0.883 | 53718 | 12/13 | 0.960 |
| P14 | 97.315338 | 29.542 | 1.108 | 24489 | 13/14 | 0.969 |
| P15 | 94.104630 | 29.642 | 1.100 | 10631 | 9/10 | 0.916 |
| P16 | 88.826569 | 32.425 | 0.767 | 2937 | 10/11 | 0.761 |
| P17 | 96.782722 | 37.992 | 1.133 | 22787 | 13/14 | 0.958 |
| TRP | 674.284607 | 42.150 | 1.583 | 277999 | 9/10 11/10 | 0.979 0.966 |

The analysis records were linked by a unique identifier to clinical data of clinical diagnosis, diagnostic criteria, age, pharmaceutical history, sex and race. Pools analyzed as samples against standards for known values were utilized to assess the precision of known compound values in the data base. Standards sequentially analyzed against identical standards were used as a measure of instrumental performance and pools sequentially analyzed against identical pools were utilized as a measure of the precision of unknown peaks.

Validation of the Data

Control standards analyzed against sequential control standards yielded precision values ranging from ±1%–±4% CV (coefficient of variation) with no outlying values. Pools analyzed as samples gave precision values ranging from ±2–±7% CV for compounds present at the 0.5 ng/mL level or greater and typically ±25–30% for compounds present at 2× the detection limit of 0.02–0.03 ng/mL (e.g. 5HT, EPI). Pools analyzed against sequential pools for unknowns gave values of ±3–±15% coefficient of variation. Typically, the coefficient of variation of the pools was 5–25 fold less than the coefficient of variation of analytes in a group of samples. Essentially, the contribution of assay variability to the results is minimal.

The data base, upon completion, contained 280 samples by 57 analytes (17,000 records). Of these, 163 were null either because no peaks were detected at the sensitivity limits of the assay, or because a signal detected did not meet the qualitative criteria for purity.

Regression Analysis

Linear regression analysis and stepwise regression analysis were used in a preliminary evaluation of the data. Both raw and mean corrected data was evaluated.

Regression comparison of the AD group (61) vs. controls (60) setting AD=1 and C=0 gave a categorical separation regression equation with an S (standard error of estimate) value=0.39 and p (the probability that the sample belongs in one group and not in another) value=0.0041 for 27 of the most significant known compound variables identified in stepwise regression (Table I). Inclusion of 7 of the most significant variables (labeled with asterisks in Table II) from the pool analysed unknown peak data base gave values of S=0.382 and p=0.0037. Assuming a clinical diagnostic error rate in the order of 10%, seven AD samples with regression calculated values (from −1.2 to 0.01) were removed from the calculation. The regression characteristics were then S=0.352 and p=0.0031.

Regression of the AD group with AD=1 vs. all others (219)=0 for the same variable group yielded an equation with S=0.481 and p=0.0013.

Observations: Although the AD group is separated from other groups with a high degree of probability, there is too high a degree of overlap for a simple linear regression algorithm to accurately categorize an individual sample.

Cluster Analysis Procedures

Cluster analysis procedures using nearest neighbor arid furthest neighbor approaches were applied to the data base. With both these approaches, the AD group tended to cluster, but controls were scattered relatively evenly, both outside and inside the AD region. Thus, the cluster analysis approach is not suitable as a categorization tool for this type of data.

Observations: The behavior of the data under cluster analysis protocols, and the observations that the standard deviations of compound values and of precursor/product ratios across metabolic pathways within a disorder group are smaller than within control groups is consistent with the hypothesis that the biochemical response of controls or normal individuals is more chaotic than that of disordered individuals.

Frequency Distribution Probability Analysis

The observations on the nature of the data distributions coupled with the technical ability to run large numbers of samples and variables offers an approach to categorization based on differences in the frequency distributions of variables in different disorder categories. This approach relies in basic probability considerations without any assumptions on the shape of a distribution curve of linearity of relationships.

The simplest question that I have investigated for the preliminary data base is that given an unknown sample, what is the probability (p) that that sample belongs in one group and not another.

For one variable, the question takes the form:

$$P = \frac{f(V_1)_A}{f(V_1)_A + f(V_1)_B}$$

where $F(V_n)_A$ or $f(V_n)_B$=the frequency with which an unknown sample value $(V_n)$ occurs in category A or category B.

For multiple compounds, the expression expands:

$$P = \frac{f(V_1)_A \cdot f(V_2)_A \ldots f(V_n)_A}{f(V_1)_A \cdot f(V)_A \ldots f(V_n)_A + f(V_1)_B \cdot f(V_1)_B \ldots f(V_n)_B}$$

If all frequencies are the same, the P value is 0.5 or a 50/50 chance that the unknown sample is A and not B. A positive answer compresses the expression to a 1 and a negative answer to 0.

Like cluster procedures and unlike regression, the use of the algorithm is independent of the number of variables used.

Implementation of the Procedure:

The implementation of the procedure is by the following steps:

1. Frequency distributions (shown in FIGS. 1a–1d) were created by using a smoothing algorithm based on a 3 point polynomial expansion function that treats each point in the sparse data distribution with equal weighting as the means of a distribution with a width at half height proportional to its value. The use of smoothing functions is a necessary assumption until the number of samples in a particular category reaches approximately 300–400. The procedure used was to divide all data in the categories by the maximum value among categories X 85, apply the polynomial expression algorithm, and normalize the data distributions for the number of samples in each category. The frequency distributions in each category are then organized into look up tables for each variable (Table IV)

TABLE IV

DISTRIBUTION TABLE

| | HVA AD | CONTROL | | MHPG AD | CONTROL |
|---|---|---|---|---|---|
| 1 | 0.010377 | 0.000205 | 1 | 1.2E-10 | 0.000000 |
| 2 | 0.045259 | 0.001702 | 2 | 0.000000 | 0.000003 |
| 3 | 0.126131 | 0.007945 | 3 | 0.000000 | 0.000026 |
| 4 | 0.242295 | 0.025793 | 4 | 0.000000 | 0.000140 |
| 5 | 0.379120 | 0.064431 | 5 | 0.000000 | 0.000576 |
| 6 | 0.503888 | 0.129976 | 6 | 0.000001 | 0.001932 |
| 38 | 0.798418 | 0.938551 | 38 | 1.117459 | 0.742461 |
| 39 | 0.761982 | 0.889793 | 39 | 1.160736 | 0.801194 |
| 40 | 0.730955 | 0.836392 | 40 | 1.196534 | 0.855713 |
| 83 | 0.006846 | 0.088021 | 83 | 0.225452 | 0.069938 |
| 84 | 0.005088 | 0.081885 | 84 | 0.208132 | 0.064130 |
| 85 | 0.003699 | 0.075893 | 85 | 0.190170 | 0.041177 |

2. A sample record such as that shown in Table 5

TABLE V

DATACASE RECORD

Figure 2:
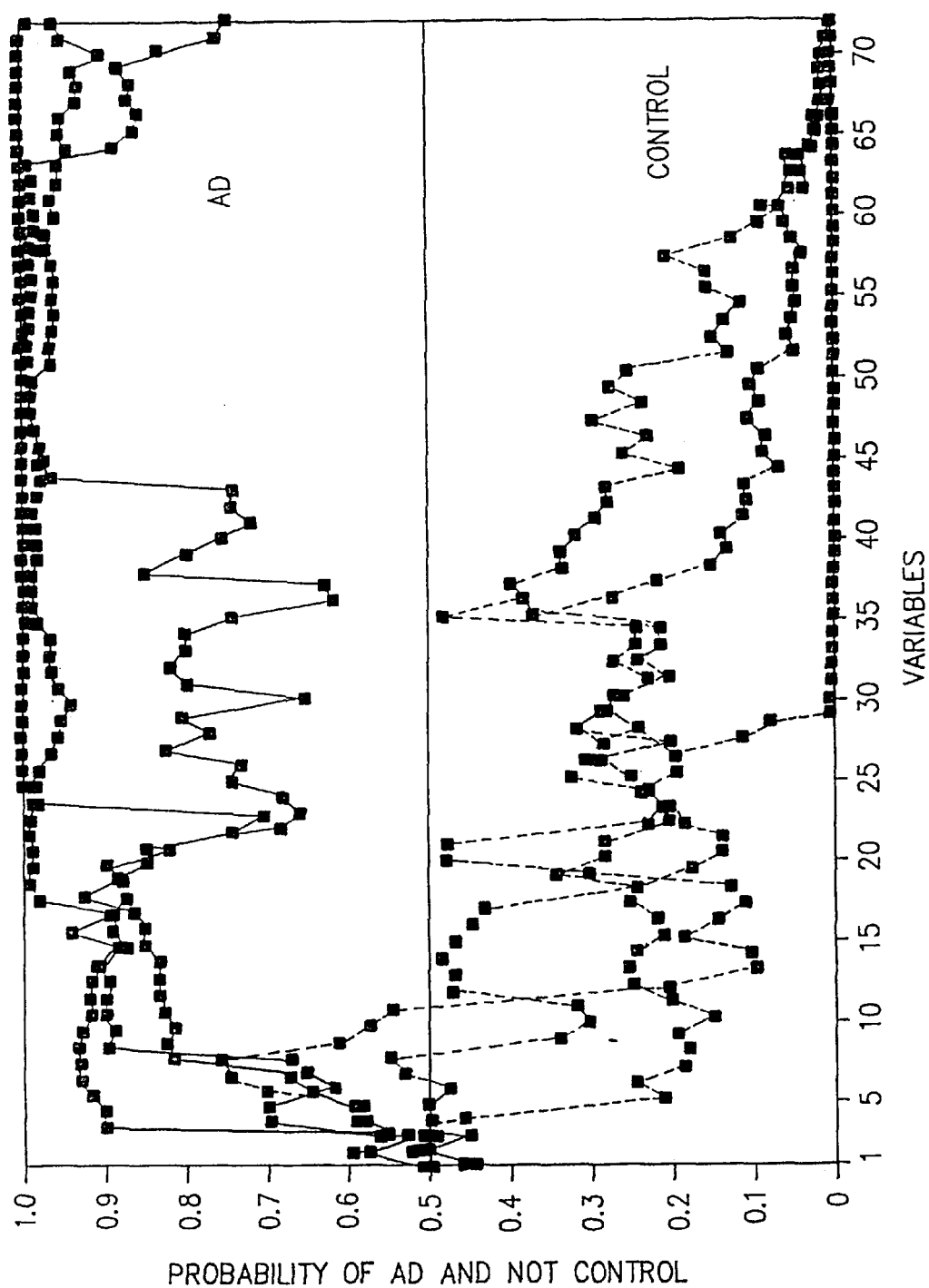
FIG. 2 is a plot showing sequential calculations.

| | C AT0022 | DISTRIBUT RANGE |
|---|---|---|
| MT3 | 0.018080 | 1 |
| OHAN3 | 0.018080 | 3 |
| OHKY3 | 0.090402 | 4 |
| 3OMD | 1.970763 | 44 |
| HVA | 58.03809 | 56 |
| MHPG | 8.714754 | 62 |
| 12 | 2911604 | 22 |
| P01 | 5725159 | 9 |
| P02 | 1359827 | 49 |
| P03 | 1808040 | 1 | is then inserted into the look up table. Individual values are divided by the range value X 85 and the frequencies for each variable for category A and B are sequentially calculated in the algorithm after subtracting the effect of that sample from the frequency table. The effect of a sequential calculation across a group of variables is shown in FIG. 2 for 3 AD and 3 C cases from a group of 61 AD and 44 controls. One of the major features of the algorithm is that no single variable predominates as a differentiation among a large group of samples.

Testing the Algorithm on AD vs. Controls

Figure 3:
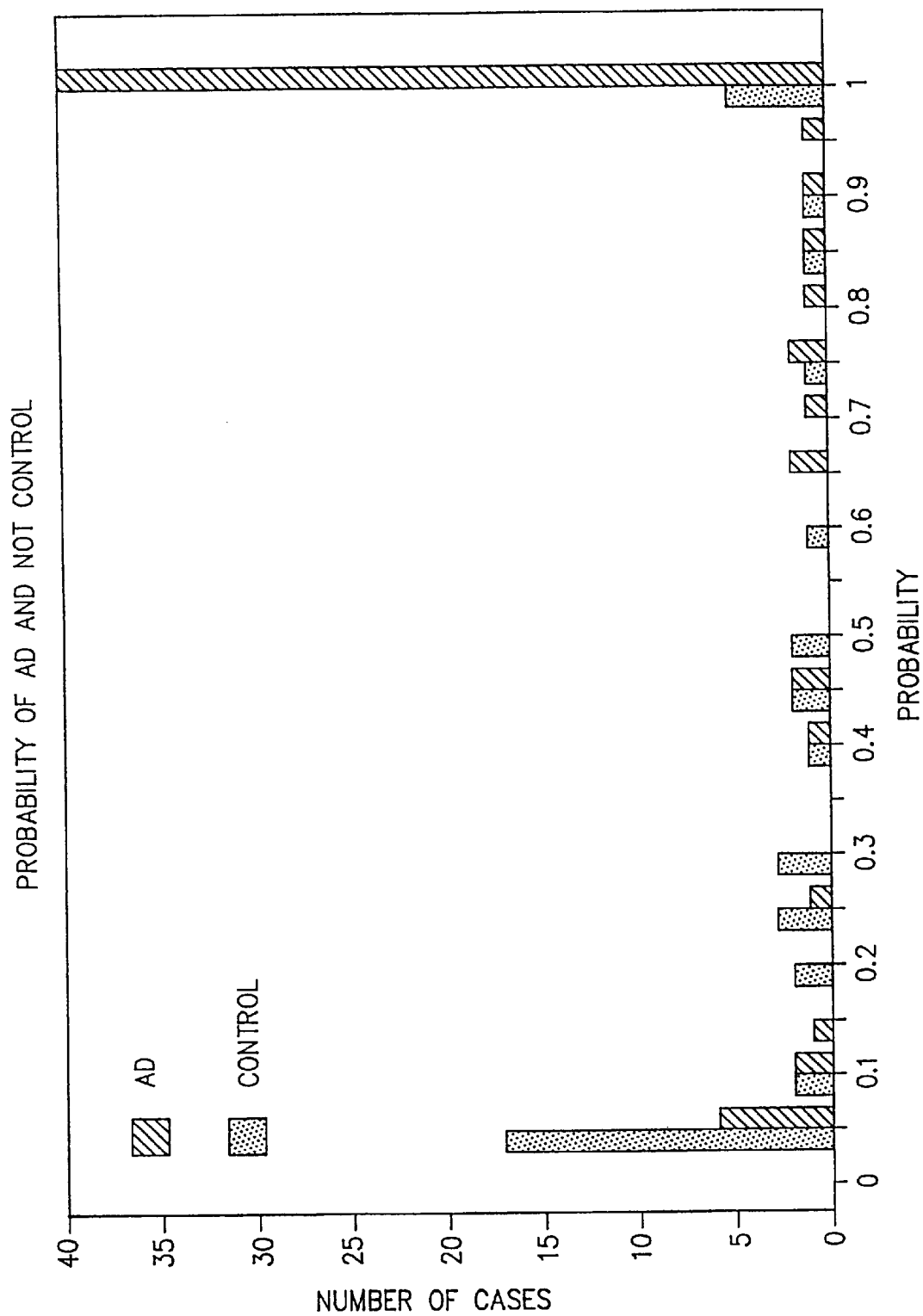
FIG. 3 is a plot showing probability analysis.

For an initial test, conditions were set up such that each individual sample was evaluated as if the data base were set up without its contribution. The results of the initial scoring are shown in FIG. 3. The scoring of five of the 61 AD cases as controls (p=less than 0.01 that the sample is an AD and not a control) is not surprising given the probable diagnostic error rate in AD. The scoring of 4 of the controls as AD are of concern.

Figure 4:
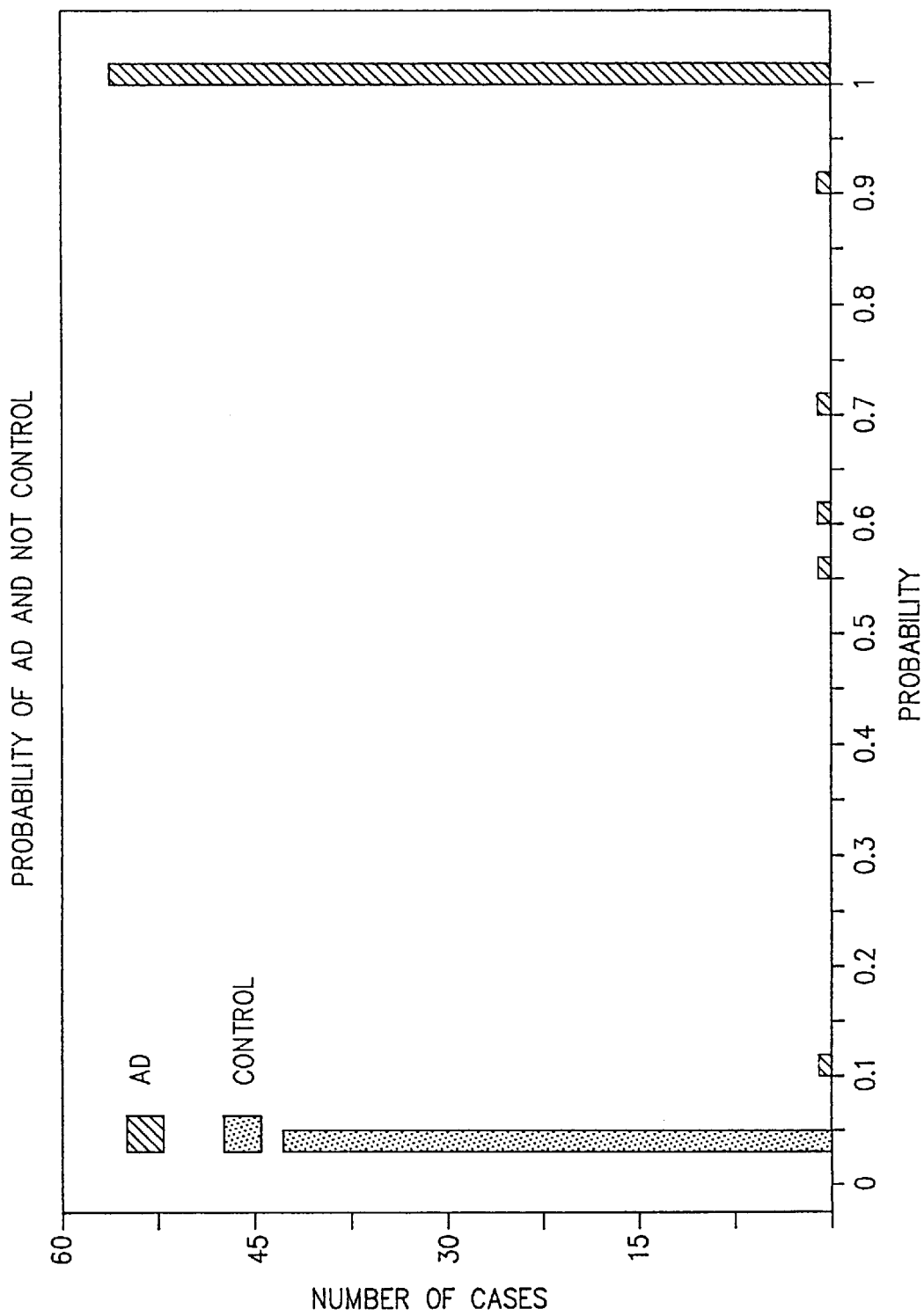
FIG. 4 is a plot similar to FIG. 3, and showing probability analysis corrected for error.

One possible explanation is that the AD data base is in effect contaminated by five cases that clearly do not match the overall AD profile and are probably not AD. When these five samples are removed from the AD data base and all samples, including the 5 removed, are scored, the control and AD groups are uniquely separated as shown in FIG. 4. The five samples that were removed from the AD scoring data group distribute in an equivocal region from 0.1 to 0.9. In subsequent application of the procedure and algorithm to AD samples vs. all other samples (PD, SC, HD, PSP and C) in the data base asking the question is this sample in the AD distribution and not in the distribution of all others yielded similar results scoring AD samples with p values=0.98 or greater. The distribution of scores of all others was scattered from 0.001 to 0.8 including the 5 AD samples which previously scored in this region vs. controls.

The invention has been described for use in diagnosing Alzheimer's Disease from CSF patient samples. It will be understood, however, that the invention advantageously may be used to diagnose and characterize other neurological, degenerative or defective disorders such as Huntington's Disease, Parkinson's Disease, schizophrenia, progressive supernuclear palsy, ALS amyotrophic lateral sclerosis (Lou Gehrig's Disease) and senile dementias. The invention also advantageously may be used to classify and diagnose tumors, carcinomas, cardiovascular abnormalities and other disorders, or for selection of therapy based on categories of known successful vs. unsuccessful outcomes. Moreover, both treatment protocols and new pharmaceuticals may be evaluated.

Still other changes and advantages will be obvious to one skilled in the art.

What is claimed is:

1. In a method for diagnosing disorders in a test individual in which fluid samples from normal, unafflicted control individuals, afflicted, abnormal individuals, and said test individual are analyzed to generate electrical signal patterns representative of molecular constituents of said samples, the improvement which comprises creating a data base of electrical signal patterns representative of frequency distribution of a plurality of predetermined molecular constituents of fluid samples from an epidemiologically significant number of individuals having known categories of disorders and from said unafflicted control individuals, and comparing said electrical signal patterns in said data base for conformity to electrical signal patterns representative of frequency distribution of said predetermined molecular constituents of a fluid sample from said test individual.

2. A method according to claim 1, wherein said fluid samples comprise a body fluid.

3. A method according to claim 2, wherein said body fluid comprises cerebrospinal fluid.

4. A method according to claim 2, wherein said body fluid comprises plasma.

5. A method according to claim 2, wherein said body fluid comprises blood containing platelets.

6. A method according to claim 2, wherein said body fluid comprises nasal mucosa.

7. A method according to claim 2, wherein said body fluid comprises serum.

8. A method according to claim 2, wherein said body fluid comprises saliva.

9. A method according to claim 2, wherein said body fluid comprises urine.

10. A method according to claim 1, wherein said fluid samples comprise electrochemically active compounds, and wherein each electrical signal pattern representative of frequency distribution of said plurality of predetermined constituents of said fluid samples is generated by the following steps, comprising: passing each one of said fluid samples separately through a liquid chromatographic column for achieving time-space separation of the electrochemically active compounds of said fluid sample eluting in the column and generating electrical signals representative of the electrochemical pattern of said fluid sample using an electrochemical detection apparatus.

11. A method according to claim 1, wherein one of said known categories of disorders comprises Alzheimer's Disease.

12. A method according to claim 1, wherein one of said known categories of disorders comprises Parkinson's Disease.

13. A method according to claim 1, wherein one of said known categories of disorders comprises Huntington's Disease.

14. A method according to claim 1, wherein one of said known categories of disorders comprises schizophrenia.

15. A method according to claim 1, wherein one of said known categories of disorders comprises Progressive Supernuclear Palsy.

16. A method according to claim 1, wherein one of said known categories of disorders comprises amyotrophic lateral sclerosis.

17. A method according to claim 1, wherein one of said known categories of disorders comprises senile dementis.

18. A method according to claim 1, wherein one of said known categories of disorders comprises tumors.

19. A method according to claim 1, wherein one of said known categories of disorders comprises carcinomas.

20. A method according to claim 1, wherein one of said known categories of disorders comprises cardiovascular abnormalities.

* * * * *